(12) United States Patent
Fujita et al.

(10) Patent No.: US 12,369,580 B2
(45) Date of Patent: Jul. 29, 2025

(54) PLANT VITALIZING AGENT CONTAINING EXOGENOUS ELICITOR AND ENDOGENOUS ELICITOR AND USE THEREOF

(71) Applicant: SHOWA DENKO K.K., Tokyo (JP)

(72) Inventors: Ichiro Fujita, Tokyo (JP); Makoto Saito, Tokyo (JP); Hiroshi Uchida, Tokyo (JP); Hisashi Kimoto, Awara (JP)

(73) Assignee: Resonac Corporation, Tokyo (JP)

( * ) Notice: Subject to any disclaimer, the term of this patent is extended or adjusted under 35 U.S.C. 154(b) by 763 days.

(21) Appl. No.: 17/619,627

(22) PCT Filed: Jun. 15, 2020

(86) PCT No.: PCT/JP2020/023467
§ 371 (c)(1),
(2) Date: Dec. 16, 2021

(87) PCT Pub. No.: WO2020/255932
PCT Pub. Date: Dec. 24, 2020

(65) Prior Publication Data
US 2022/0354116 A1    Nov. 10, 2022

(30) Foreign Application Priority Data
Jun. 17, 2019 (JP) ................................. 2019-112187

(51) Int. Cl.
*A01N 43/16* (2006.01)
*A01G 7/06* (2006.01)
*C12Q 1/00* (2006.01)

(52) U.S. Cl.
CPC .............. *A01N 43/16* (2013.01); *A01G 7/06* (2013.01); *C12Q 1/00* (2013.01)

(58) Field of Classification Search
CPC .................................. A01N 43/16; A01G 7/06
See application file for complete search history.

(56) References Cited

U.S. PATENT DOCUMENTS

| | | | |
|---|---|---|---|
| 4,099,267 A * | 7/1978 | King | B01F 23/53 366/172.1 |
| 5,043,007 A * | 8/1991 | Davis | C05G 5/30 71/31 |
| 5,588,254 A | 12/1996 | Adachi et al. | |
| 6,460,290 B1 * | 10/2002 | Moore | C05G 3/70 71/64.1 |
| 2006/0121126 A1 * | 6/2006 | McFadden | A01N 65/00 514/26 |
| 2008/0072494 A1 | 3/2008 | Stoner et al. | |
| 2018/0362669 A1 | 12/2018 | Fujita et al. | |

FOREIGN PATENT DOCUMENTS

| | | | |
|---|---|---|---|
| CN | 103508824 A | 1/2014 | |
| CN | 103548829 A | 2/2014 | |
| CN | 109438137 A | 3/2019 | |
| EP | 2 524 597 A1 | 11/2012 | |
| JP | 63-215606 A | 9/1988 | |
| JP | 6-17282 B2 | 3/1994 | |
| JP | 09-143013 A | 6/1997 | |
| JP | 9-315907 A | 12/1997 | |
| JP | 2001-017176 A | 1/2001 | |
| JP | 2001-064112 A | 3/2001 | |
| JP | 2002-144610 A | 5/2002 | |
| JP | 2013-151438 A | 8/2013 | |
| JP | 2015-048436 A | 3/2015 | |
| JP | 2017-095352 A | 6/2017 | |
| WO | 2011/087002 A1 | 7/2011 | |
| WO | 2012/046758 A1 | 4/2012 | |
| WO | WO-2015059864 A1 * | 4/2015 | ............. B01J 2/003 |
| WO | 2017/104687 A1 | 6/2017 | |

OTHER PUBLICATIONS

Mandelman et al., "X-Ray Crystal Structure of the Multidomain Endoglucanase Cel9G from Clostridium cellulolyticum Complexed with Natural and Synthetic Cello-Oligosaccharides", Jul. 2003, Journal of Bacteriology, vol. 185, No. 14, pp. 4127-4135. (Year: 2003).*
Vazquez et al., "Xylooligosaccharides: manufacture and applications", 2000, Trends in Food Science & Technology, vol. 11, pp. 387-393. (Year: 2000).*
English machine translation of WO 2015/059864 A1 made Aug. 19, 2024. (Year: 2024).*
International Search Report for PCT/JP2020/023467 dated Sep. 8, 2020 [PCT/ISA/210].

* cited by examiner

*Primary Examiner* — Michael B. Pallay
(74) *Attorney, Agent, or Firm* — Sughrue Mion, PLLC

(57) ABSTRACT

Physiological processes in plants are regulated and reinforced, and crop vitality, yield, quality and post-harvesting storage life are improved. A plant vitalizer comprising an exogenous elicitor and an endogenous elicitor is applied to plants.

12 Claims, No Drawings

PLANT VITALIZING AGENT CONTAINING EXOGENOUS ELICITOR AND ENDOGENOUS ELICITOR AND USE THEREOF

CROSS REFERENCE TO RELATED APPLICATIONS

This application is a National Stage of International Application No. PCT/JP2020/023467 filed on Jun. 15, 2020, claiming priority based on Japanese Patent Application No. 2019-112187 filed on Jun. 17, 2019.

FIELD

The present invention relates to a plant vitalizer comprising an exogenous elicitor and an endogenous elicitor, as well as a method for cultivating and producing a plant using the plant vitalizer.

BACKGROUND

Plants suffer reduction in yields due to abiotic stress including daylight hours, atmospheric temperature and rainfall, and biological stress such as pests. Various types of fertilizers and agricultural chemicals have been used in the prior art to increase yields, especially of agricultural crops. Fertilizers are nutrients that are required for plant growth, but they lack functions for alleviating stress. Agricultural chemicals directly eliminate pests that parasitize plants and thus eliminate biological stress, but the safety of using agricultural chemicals has not been adequately confirmed, and concerns remain regarding the effects of their excess consumption on the human body and on the environment, while chemical agents such as agricultural chemicals produced by chemical synthesis methods are especially concerning in terms of their dispersion and residence for long periods in soil, and consequently other methods are desired to provide resistance against biological stress. The use of biostimulants has also been a subject of interest in recent years, since they are substances that are safe for the human body and the environment.

The term "biostimulant", sometimes synonymous with "plant vitalizer", refers to a component that contains a substance group or microorganism and, when applied to the plant body or its root system, stimulates the series of processes that take place in the plant body in its natural state, thereby improving nutrient absorption, increasing fertilization efficiency, providing stress resistance and improving quality, while not having a direct effect against pests so that it is not classified as an insecticide or microbicide. In other words, it is a component found in the natural world (including microorganisms), as a substance which is not a plant hormone or nutrient but, even in small amounts, stimulates plant activity and promotes growth. Applying a biostimulant to a plant increases nutrient absorption and nutrient utilization in the plant, promoting its growth and improving the yield and quality of crops. Agriculture biostimulants include various formulations such as compounds, substances or other products that act on plants or soil to regulate and reinforce physiological processes in crops. Biostimulants act on plant physiology by a different route than that of nutrients to improve crop vitality, yield, quality and post-harvesting storage life.

Biostimulants can therefore stimulate the innate abilities of plants and promote their growth without causing problems associated with conventional agricultural chemicals or fertilizers.

Previous publications related to such biostimulants have contained descriptions of: plant vitalizers that combine chitin oligosaccharides with chitosan which has antimicrobial activity (PTL 1), plant vitalizers combining oligosaccharides and plant extract components in vinegar (PTL 2), plant growth accelerators that include cellulose (PTL 3), plant growth regulators that include hexofuranose derivatives (PTL 4), a method of increasing plant disease resistance using low molecularized chitin or chitosan (PTL 5), and fertilizers containing chitin and/or chitosan (PTL 6).

CITATION LIST

PATENT LITERATURE

[PTL 1] Japanese Unexamined Patent Publication HEI No. 9-143013
[PTL 2] Japanese Unexamined Patent Publication No. 2001-64112
[PTL 3] Japanese Unexamined Patent Publication No. 2002-114610
[PTL 4] Japanese Unexamined Patent Publication No. 2013-151438
[PTL 5] Japanese Unexamined Patent Publication No. 2015-48436
[PTL 6] Japanese Unexamined Patent Publication No. 2017-95352
[PTL 7] International Patent Publication No. 2017/104687

SUMMARY

Technical Problem

The problem to be solved by the invention is to regulate and reinforce physiological processes in plants, and improve crop vitality, yield, quality and post-harvesting storage life.

Solution to Problem

As a result of diligent research and experimentation with the aim of solving this problem, the present inventors have completed this invention upon finding, surprisingly, that a combination of an exogenous elicitor and an endogenous elicitor promotes plant growth and increases elicitor activity for the plant.

Specifically, the present invention provides the following.

[1] A plant vitalizer comprising an exogenous elicitor and an endogenous elicitor.

[2] The plant vitalizer according to [1], wherein the exogenous elicitor is a chitin oligosaccharide, and the endogenous elicitor is at least one type of oligosaccharide selected from among cellooligosaccharides and xylooligosaccharides.

[3] The plant vitalizer according to [1] or [2], wherein the total content of the exogenous elicitor and the endogenous elicitor in the plant vitalizer is 0.05 to 10 mass %.

[4] The plant vitalizer according to any one of [1] to [3], wherein the mass ratio of the exogenous elicitor with respect to the endogenous elicitor in the plant vitalizer is 0.2 to 5.

[5] The plant vitalizer according to any one of [1] to [4], which comprises a xylooligosaccharide as the endogenous elicitor.

[6] The plant vitalizer according to [5], which comprises both a cellooligosaccharide and a xylooligosaccharide as the endogenous elicitor.

[7] The plant vitalizer according to [6], wherein the mass ratio of the cellooligosaccharide with respect to the xylooligosaccharide in the plant vitalizer is 0.2 to 5.

[8] The plant vitalizer according to any one of [1] to [7], which further comprises a spreading agent.

[9] A plant cultivation method, which comprises applying a plant vitalizer according to any one of [1] to [8] to a plant.

[10] The method according to [9], which comprises applying the plant vitalizer to a plant at a concentration so that the total content of the exogenous elicitor and the endogenous elicitor is 0.1 to 500 ppm by mass.

[11] The method according to [9] or [10], wherein the plant vitalizer is applied to the plant by foliar application.

[12] A method of producing a plant or a part thereof having increased elicitor activity compared to the same without application of a plant vitalizer according to any one of [1] to [8], wherein the method comprises cultivating the plant by the method according to any one of [9] to [11].

[13] The method according to [12], wherein the elicitor activity is determined by measuring glucanase production in the plant.

[14] A fertilizer composition comprising a plant vitalizer according to any one of [1] to [8].

Advantageous Effects of Invention

According to the invention it is possible to regulate and reinforce physiological processes in plants without causing problems such as effects on the human body or environment as are caused by conventional agricultural chemicals or fertilizers, and to improve crop vitality, yield, quality and post-harvesting storage life.

DESCRIPTION OF EMBODIMENTS

According to a first aspect of the invention there is provided a plant vitalizer comprising an exogenous elicitor and an endogenous elicitor.

The term "plant vitalizer" according to the invention includes not only substances that have effects of alleviating abiotic stresses such as temperature, light, water and salts that are involved in the growth of plants, but also effects of alleviating biological stresses such as pests.

The term "elicitor" generally refers to a substance that induces a biological defense reaction in a higher plant tissue or cultured cells, whereby it induces disease resistance by plant immunomechanisms. Plants are sensitive to elicitors by receptors present on leaf surfaces, initiating pathogen resistance reactions. This induces biological defense activity (immunity) in which various compounds are secreted against different pathogenic organisms. When an elicitor acts on a plant, it induces defense reactions such as synthesis and accumulation of phytoalexins and infection-specific proteins, production of active oxygen species, production of active nitrogen species, hypersensitive reactive cell death, and changes in gene expression, these reactions being thought to protect the plant from pathogenic organisms and increase disease resistance.

Phytoalexins are antimicrobial compounds synthesized and accumulated in the plant body due to action of elicitors, and the antimicrobial compounds produced differ depending on the plant variety. Typical phytoalexins include flavonoids, terpenoids and fatty acid derivatives. Active oxygen species have activity that kills pathogenic microorganisms, while active oxygen and active nitrogen species, either alone or in coordination, function as signals to initiate various defense reactions. The disease resistance provided by such elicitor effects helps to augment resistance against a wide range of diseases, and it is therefore expected to be useful for agriculture.

Throughout the present specification, "exogenous elicitor" means an elicitor which is a substance derived from an organism other than the plant, such as a fungus, insect or crustacean, and while it is not particularly restricted so long as it has an elicitor effect, it will typically be chitin, chitosan or one of their oligosaccharides, or insect-derived biomolecules.

The plant vitalizer of the invention preferably comprises a chitin oligosaccharide as the exogenous elicitor.

Chitin oligosaccharides contain partially deacetylated chitosan oligosaccharides, being oligosaccharides with several N-acetylglucosamines linked together, which can generally be obtained by hydrolysis of crustacean-derived chitins, and they are also known as oligo-N-acetylglucosamines.

Specifically, chitin oligosaccharides are obtained by chemical or enzymatic partial hydrolysis of chitin prepared by a common method from shells of crustaceans such as crab or shrimp. A chitin oligosaccharide that is used is preferably one or a mixture of more than one selected from among N-acetylchitobiose, N-acetylchitotriose, N-acetylchitotetraose, N-acetylchitopentaose, N-acetylchitohexaose, N-acetylchitoheptaose and N-acetylchitooctaose. Among these, N-acetylchitopentaose, N-acetylchitohexaose and N-acetylchitoheptaose have particularly high elicitor effects.

Chitin oligosaccharides to be used for the invention are most preferably ones having the following chemical structure.

[Chemical Formula 1]

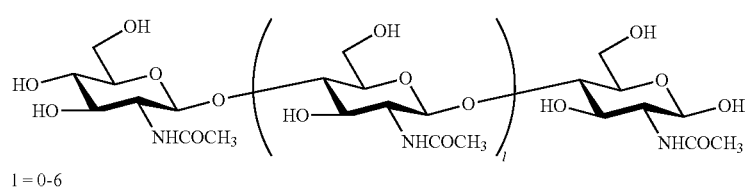

l = 0-6

These include compounds wherein some of the acetyl groups ($COCH_3$) are shed, leaving $NH_2$ groups. The percentage of deacetylation is preferably no greater than 30%, more preferably no greater than 20% and even more preferably no greater than 15% of the total chitin oligosaccharide.

Throughout the present specification, "endogenous elicitor" means a plant-derived elicitor, with no particular restrictions so long as it has an elicitor effect, but typically it will be a cellulose or xylan produced from a plant, or an oligosaccharide of the same.

The plant vitalizer of the invention preferably comprises at least one oligosaccharide selected from among cellooligosaccharides and xylooligosaccharides, as an endogenous elicitor.

Cellooligosaccharides are oligosaccharides polymerized by β-glycoside bonding of multiple glucose molecules, and in recent years they have been found to have functionality including moisture retention, stickiness inhibition, freshness functionality, starch aging reduction and protein denaturation inhibition, for which they are expected to have uses in the fields of medicine, cosmetics, foods and feed. In particular, cellooligosaccharides with a glucose polymerization degree of 3 or greater are even more promising in terms of increasing the functionality mentioned above and also providing new functionality. The cellooligosaccharides currently used in industry are produced by enzyme reaction, but their main components are glucose and dimeric cellobioses, whereas they contain almost no trimeric cellotriose or greater oligomers. In recent years, however, the present applicants have reported a method for producing cellooligosaccharides that comprise oligomers with a glucose polymerization degree of 3 to 6, in hydrolysis reaction of vegetable biomass using a carbon catalyst, by carrying out hydrothermal reaction while controlling the temperature-elevating rate, cooling rate, reaction temperature and reaction time (PTL 7).

When a cellooligosaccharide is to be obtained by hydrolysis of cellulose, it is preferred to use crystalline fine powdered cellulose such as AVICEL (product of Merck), or cotton linter pulp, as the cellulose starting material.

Cellooligosaccharides to be used for the invention are most preferably ones having the following chemical structure.

a stock solution comprising the exogenous elicitor and endogenous elicitor dissolved at high concentration in a solvent such as water. As one embodiment, the total content of the exogenous elicitor and endogenous elicitor in the plant vitalizer stock solution is preferably 0.05 to 10 mass %, more preferably 0.1 to 8 mass % and even more preferably 0.5 to 6 mass %. As another embodiment, the total content of the exogenous elicitor and endogenous elicitor in the plant vitalizer stock solution is preferably 1 to 15 mass %, more preferably 3 to 12 mass % and even more preferably 5 to 10 mass %.

As one embodiment, the mass ratio of the exogenous elicitor with respect to the endogenous elicitor in the plant vitalizer of the invention (exogenous elicitor content/endogenous elicitor content) is preferably 0.2 to 5, more preferably 0.3 to 3 and even more preferably 0.5 to 1.5. As another embodiment, the total mass ratio of the exogenous elicitor with respect to the endogenous elicitor is preferably 0.1 to 4, more preferably 0.2 to 2 and even more preferably 0.3 to 1.

The plant vitalizer of the invention more preferably comprises a xylooligosaccharide as the endogenous elicitor, and optimally it comprises both a cellooligosaccharide and a xylooligosaccharide. As one embodiment, the mass ratio of the cellooligosaccharide with respect to the xylooligosaccharide in the plant vitalizer of the invention (cellooligosaccharide content/xylooligosaccharide content) is preferably 0.2 to 5, more preferably 0.3 to 3 and even more preferably 0.5 to 1.5. As another embodiment, the mass ratio of the cellooligosaccharide with respect to the xylooligosaccharide is preferably 0.1 to 4, more preferably 0.2 to 2 and even more preferably 0.3 to 1.

[Chemical Formula 2]

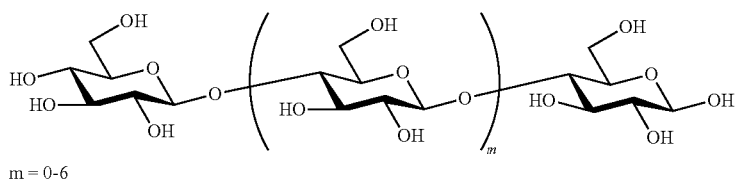

m = 0-6

Xylooligosaccharides are oligosaccharides polymerized by β-glycoside bonding of multiple xylose molecules, and they are generally obtained by hydrolysis of xylan as the main component of hemicellulose, being marketed mainly for comestible purposes.

Xylooligosaccharides to be used for the invention are most preferably ones having the following chemical structure.

When the plant vitalizer comprises a chitin oligosaccharide as the exogenous elicitor and both a cellooligosaccharide and a xylooligosaccharide as the endogenous elicitor, the percentage of each oligosaccharide with respect to the total content of the chitin oligosaccharide, cellooligosaccharide and xylooligosaccharide is preferably 10 to 50 mass % of the chitin oligosaccharide, 10 to 50 mass % of the cellooligosaccharide and 10 to 60 mass % of the xylooli-

[Chemical Formula 3]

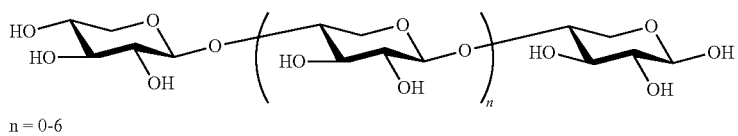

n = 0-6

The plant vitalizer of the invention may be prepared as a product in any form such as powder, granules or liquid, but it is generally preferred to be in easily dispersible liquid form. The plant vitalizer of the invention can be supplied as gosaccharide. The percentage of each oligosaccharide is more preferably 20 to 40 mass % of the chitin oligosaccharide, 20 to 40 mass % of the cellooligosaccharide and 20 to 55 mass % of the xylooligosaccharide.

The plant vitalizer of the invention may also contain components other than the exogenous elicitor and endogenous elicitor as active components, such as antiseptic agents, spreading agents, anti-settling agents, thickeners and fillers. Antiseptic agents include potassium sorbate, paraoxybenzoic acid esters, benzoin, sodium dehydroacetate, hinokitiol, phenoxyethanol, polyaminopropyl biguanide and polylysine. Spreading agents are viscous liquids composed mainly of surfactants, and they are not particularly restricted so long as they can be used as spreading agents for plant vitalizers, examples including polyoxyethylene nonylphenyl ethers, sorbitan fatty acid esters and polyoxyethylene hexitan fatty acid esters. Anti-settling agents include polyphosphoric acid and polyphosphoric acid salts, or polycarboxylic acid-type polymer surfactants. Thickeners include carboxymethyl cellulose (CMC), polyacrylamide, water-soluble polymers such as starch, or molasses, alcohol fermentation concentrate waste liquids and amino acid fermentation concentrate waste liquids. Fillers include lactose and starch.

According to a second aspect of the invention there is provided a plant cultivation method that comprises applying a plant vitalizer of the invention to a plant.

Plants to which a plant vitalizer of the invention is to be applied are not particularly restricted but will typically be crops, such as plants of the family Compositae, Solanaceae, Brassicaceae, Poaceae, Leguminosae, Rosaceae, Cucurbitaceae, Convolvulaceae, Chenopodiaceae, Liliaceae, Umbelliferae, Malvaceae, Zingiberaceae or Nelumbonaceae.

Specifically, these include Brassicaceae plants such as Chinese cabbage, cabbage, broccoli, cauliflower, komatsuna, mizuna, Japanese radish and turnip, Solanaceae plants such as potato, tomato, eggplant, bell pepper, capsicum, shishito and tobacco, Compositae plants such as crowndaisy, lettuce, leaf lettuce, burdock and butterbur, Cucurbitaceae plants such as watermelon, melon, pumpkin, cucumber, nigauri, loofah and gourd, Chenopodiaceae plants such as spinach, chard, Swiss chard, okahijiki and beet, Umbelliferae plants such as ginseng, celery, parsley and mitsuba, Leguminosae plants such as soybean (green soybean), adzuki bean, green bean, horse-bean, pea, winged-bean and peanut, Convolvulaceae plants such as sweet potato and water spinach, Liliaceae plants such as Chinese chive, Welsh onion, onion, garlic and asparagus, Rosaceae plants such as strawberry, apple, pear and loquat, Malvaceae plants such as okra and cotton, Zingiberaceae plants such as ginger, Nelumbonaceae plants such as lotus, and Poaceae plants such as corn, rice, barley, wheat and sugarcane.

Of these, Brassicaceae plants such as cabbage and komatsuna, Solanaceae plants such as tomato and eggplant, Compositae plants such as lettuce and leaf lettuce and Rosaceae plants such as strawberry and apple are preferred, with komatsuna and tomato being more preferred.

The plant vitalizer of the invention will generally be used after dilution to a desired concentration (such as 1000-fold dilution) by addition of water or the like to the stock solution, and applied to a plant at a concentration so that the total content of the exogenous elicitor and the endogenous elicitor in the plant vitalizer is preferably 0.1 to 500 ppm by mass. It may also be applied to a plant in a concentration so that the total content of the exogenous elicitor and endogenous elicitor in the plant vitalizer is preferably 0.5 to 200 ppm by mass and more preferably 1 to 100 ppm by mass.

Application of the plant vitalizer to a plant may be by any method commonly used by those skilled in the art without any particular restriction on the dispersion method, examples including a method of direct dispersion onto the leaves or stems of the plant, a method of dispersion into culture medium or soil in which the plant is to be cultivated, or a method of mixing into fertilizer and then dispersion into culture medium or soil. For mixing into fertilizer, the type of fertilizer is not restricted and may be chemical fertilizer comprising nitrogen, phosphoric acid and potassium, or organic fertilizer containing oil residue, fish residue, bone powder, sea weed powder, amino acids, saccharides or vitamins. The dispersion method is preferably carried out by foliar application, as this will allow the elicitor activity to be effectively exhibited. Foliar application may be carried out by a method commonly known to those skilled in the art, using a mechanical power atomizer, shoulder atomizer, broadcaster, sprayer, manned or unmanned helicopter, duster or hand sprayer.

When the plant vitalizer is to be dispersed after mixing with a fertilizer, the content of the exogenous elicitor is preferably 5 to 30 mass % and more preferably 8 to 20 mass %, with respect to 100% solid mass of the fertilizer composition. The content of the endogenous elicitor is preferably 15 to 60 mass % and more preferably 25 to 50 mass %, with respect to 100% solid mass of the fertilizer composition. The fertilizer composition more preferably also comprises at least one nutrient selected from among nitrogen, phosphoric acid and potassium, and more preferably comprises all three nutrients nitrogen, phosphoric acid and potassium, in addition to the exogenous elicitor and endogenous elicitor. In the case of a liquid fertilizer, the fertilizer composition contains water at preferably 70 to 99 mass % and more preferably 75 to 99 mass %, and preferably the stock solution is diluted 100-fold to 1000-fold before dispersion.

By cultivating the plant using this method, it is possible to produce a plant or a part thereof (for example, root, stem, leaf, flower, fruit, seed, tissue or cells) having elicitor activity compared to the same without application of a plant vitalizer, and to thus improve crop vitality, yield, quality and post-harvesting storage life.

As mentioned above, the elicitor effect is important as one index of disease resistance, but the present inventors have found that the elicitor activity can be evaluated based on glucanase production, as a signal of the elicitor effect, by measuring its enzyme activity. A portion of the leaves of a plant being cultivated may be harvested to analyze the glucanase activity, allowing periodic evaluation of the same individual.

The following is a summary of the procedure for a method of evaluating elicitor activity: (i) The plant is sampled and pretreated; (ii) a calibration curve is drawn using BSA as the protein standard (using absorbance at a wavelength (600 nm) in a dye binding method); (iii) the protein concentration of the specimen prepared in (i) is measured; (iv) the glucanase activity of the specimen prepared in (i) is measured. Specifically, the activity is evaluated as the absorbance value at a wavelength of 590 nm, using a B-HS reagent that exhibits color when soluble low molecular decomposition products are freed by glucanase; and (v) the glucanase activity is calculated in terms of protein units.

The specific procedure for evaluation of the elicitor activity is explained in detail below in the Examples.

These Examples serve merely for concrete illustration of the invention and are not intended to be limitative on the invention.

EXAMPLES

1. Preparation of Oligosaccharides (1) Chitin Oligosaccharide

A 10 g portion of chitin (purified chitin by FujiFilm-Wako Pure Chemical Industries) was dispersed in 30 mL of water containing 1.2 g of phosphoric acid, the powder that had been dried under reduced pressure was placed in a 250 mL-volume alumina pot together with 100 g of alumina balls with diameters of 5 mm, and then this was set in a planetary ball mill (PULVERISETTE6 by Fritsch Co.) and treatment was carried out continuously for 6 hours at 500 rpm to obtain a reaction product. The temperature was initially room temperature, and temperature increase was allowed to proceed by shear heat release.

The reaction product was then suspended in water, and after neutralizing with calcium hydroxide, the resulting slurry solution was filtered with a Nutsche filter using 5B filter paper, and the recovered filtrate was freeze-dried to obtain the chitin oligosaccharide powder.

(2) Cellooligosaccharide

The cellooligosaccharide produced by "Production method 1" was used in Examples 1 to 7 and Comparative Examples 9, 10 and 15, and the cellooligosaccharide produced by "Production method 2" was used in Examples 9, 10, 12, 14, 16 and 17.

Production method 1: From Crystalline Fine Powder Cellulose

A 10 g portion of AVICEL (crystalline fine powder cellulose by Merck) and 1.5 g of BA50 active carbon (product of Ajinomoto Fine-Techno Co. Inc.) were placed in a 3600 mL-volume ceramic pot mill together with 2000 g of alumina spheres with diameters of 1.5 cm, and this was set in a desktop pot mill rotating table (ANZ-51S Desktop Pot Mill by Nitto Kagaku Co., Ltd.), carrying out treatment for 48 hours at 60 rpm to obtain a reaction starting material. The temperature was initially room temperature, and temperature increase was allowed to proceed by shear heat release.

Next, 0.374 g of the reaction starting material and 40 mL of water were placed in a high pressure reactor (100 mL internal volume, autoclave by OM Labotech Co., hastelloy C22), after which it was heated to a reaction temperature of 230° C. at 10 to 30° C./min (average temperature-elevating rate: 11.3° C./min) while stirring at 600 rpm, the heating was abruptly stopped, and the reactor was air-cooled at 10 to 30° C./min (average temperature-lowering rate: 16.7° C./min) to prepare a reaction mixture.

Supernatant recovered from the reaction mixture using a centrifuge apparatus was then freeze-dried to obtain cellooligosaccharide powder.

Production Method 2: From Cotton Linter Pulp

A 271 g portion (1.8% water content, 266 g dry mass) of cotton linter pulp (cellulose content: 97%, Tokokosen Corp.) was mixed with 38 g of 85 mass % phosphoric acid (special grade reagent, product of FujiFilm-Wako Pure Chemical Industries) using a food blender (Model: HBF500S by Hamilton Beach Co.), to obtain 309 g of a reaction starting material (3.4% water content, phosphoric acid content: 10.4%).

Next, the 309 g of reaction starting material was loaded into a vibrating mill (device name: MB-1, product of Chuo Kakohki Co., Ltd., 5 L pot size), together with 13 kg of $\varphi\frac{3}{4}$-inch carbon steel balls, and subjected to hydrolysis by dry grinding for 24 hours under conditions with a total amplitude of 8 mm, a vibrational frequency of 16.2 Hz and a jacket circulation water temperature of 75° C., after which the reaction powder was recovered.

After then placing 10 g of the reaction powder and 90 g of ion-exchanged water in a 200 L beaker, a magnetic stirrer was used for 1 hour of stirring at 25° C. to obtain a cellulose hydrolysate extract.

Next, 1.3 g of a 40 mass % aqueous calcium hydroxide solution was added to the extract, and a magnetic stirrer was used for 1 hour of stirring at 25° C. to prepare a neutral solution, collecting the supernatant using a centrifuge apparatus and freeze-drying it to obtain cellooligosaccharide powder.

(3) Xylooligosaccharide

The xylooligosaccharide listed below under "Commercial product" was used in Examples 1 to 8 and Comparative Examples 11, 12 and 16, and the xylooligosaccharide produced by "Production method" was used in Examples 9 to 15, 17 and 18.

Production Method: From Corn Cob Powder

*Acremonium cellulolyticus* TN (FERM P-18508) was shake cultured for 6 days at 30° C. in a 500 mL flask containing 100 mL of liquid medium (50 g/L AVICEL, 24 g/L $KH_2O_4$, 5 g/L ammonium sulfate, 4.7 g/L potassium tartrate $\frac{1}{2}H_2O$, 4 g/L urea, 1 g/L Tween80, 1.2 g/L $MgSO_4\cdot7H_2O$, 10 mg/L $ZnSO_4\cdot7H_2O$, 10 mg/L $MnSO_4\cdot5H_2O$, 10 mg/L $CuSO_4\cdot5H_2O$), and then 5 g of corn cob powder suspended in 50 mL of centrifuged supernatant of the obtained culture solution was stirred and reacted at 50° C. for 72 hr, and the centrifuged supernatant of the reaction mixture was freeze-dried to obtain xylooligosaccharide powder.

Commercial Product

Xylooligosaccharide 95P by B Food Science Co., Ltd. was used.

2. Measurement of Edible Harvest and Root Dry Weight of Frill Lettuce (1) Preparation of Plant Vitalizer Each oligosaccharide prepared in [1. Preparation of oligosaccharide] was dissolved in water while stirring with a stirrer in a compositional ratio to 1000 times the plant vitalizer concentration (ppm by mass) in Examples 1 and 9 to 11 listed in the tables, after which the bacteria were removed with a 0.45 μm filter, to obtain plant vitalizer stock solutions.

(2) Cultivation Test

In the test groups, 150 g of each of the plant vitalizer stock solutions under different conditions was added to and dispersed in 150 L of culture solution prepared for hydroponics (1000-fold dilution), and cultivation was started for each of 120 varieties at a temperature of 20 to 22° C. Cultivation was carried out for a total of 60 days, adding 150 g more of plant vitalizer stock solution each week after starting, for a total of 5 times, measuring the edible harvest and root dry weight of frill lettuce, and comparing it to the same without application of the plant vitalizer (Comparative Example 1).

The edible harvest was measured by cutting the root portions and measuring the top parts as the edible portions, while the root dry weight was measured by drying the cut root parts with a constant temperature dryer at 50° C. for 12 hours and then measuring the weight.

TABLE 1

|  |  |  | Comp. Example 1 | Example 1 | Example 9 | Example 10 | Example 11 |
|---|---|---|---|---|---|---|---|
| Conditions | Plant vitalizer concentration (ppm by mass) |  | 0 | 50 | 50 | 100 | 100 |
|  | Compositional ratio | Exogenous elicitor Chitinoligosaccharide | — | 33% | 25% | 25% | 25% |
|  |  | Endogenous elicitor Cellooligosaccharide | — | 33% | 25% | 25% | — |
|  |  | Xylooligosaccharide | — | 33% | 50% | 50% | 75% |
| Results | Edible harvest (g/variety, measured count = 32) |  | 114.6 100% | 159.2 139% | 161.3 141% | 172.8 151% | 164.2 143% |
|  | Root dry weight (g/variety, measured count = 5) |  | 0.166 100% | 0.181 109% | 0.179 108% | 0.196 118% | 0.177 107% |

3. Measurement of Tomato Edible Harvest and Sugar Content (1) Preparation of Plant Vitalizer Each oligosaccharide prepared in [1. Preparation of oligosaccharide] was dissolved in water while stirring with a stirrer in a compositional ratio to 1000 times the plant vitalizer concentration (ppm by mass) in Comparative Example 3-6 and Examples 2-3 and 12-13 listed in the tables, after which the bacteria were removed with a 0.45 μm filter, to obtain plant vitalizer stock solutions. The stock solution was diluted 1000-fold with water and used for the following cultivation test.

(2) Cultivation Test

One day before field planting, the plant vitalizer solution was liberally dispersed onto medium tomato seedling leaves raised in a pot, contacting the leaf surfaces and also the pot soil.

The tomato field cultivation was in a vinyl greenhouse, with a total field area of 334 m², planting 40 medium tomato seedlings per group at 50 cm spacings, by a conventional agricultural method using chemical fertilizer.

Aqueous solutions were prepared to the concentrations of plant vitalizer for each condition, with 1.5 kg/group each time, and two weeks after planting, a procedure of foliar application and watering of the soil near the roots using a watering can was carried out once every 2 weeks for 2 months for a total of 5 times, after which the edible harvest and sugar content were measured and compared to the same without application of the plant vitalizer (Comparative Example 2).

The edible harvest was measured by cutting off only the tomato fruit as the edible part and measuring the weight directly, while the sugar content was measured by squeezing the tomato fruit juice and measuring it using a refractometer.

TABLE 2

|  |  |  | Comp. Example 2 | Comp. Example 3 | Comp. Example 4 | Comp. Example 5 | Comp. Example 6 | Example 2 | Example 3 | Example 12 | Example 13 |
|---|---|---|---|---|---|---|---|---|---|---|---|
| Conditions | Plant vitalizer concentration (ppm by mass) |  | 0 | 20 | 100 | 20 | 100 | 20 | 100 | 50 | 50 |
|  | Compositional ratio | Exogenous elicitor Chitin oligosaccharide | — | 100% | 100% | — | — | 33% | 33% | 25% | 25% |
|  |  | Endogenous elicitor Cellooligosaccharide | — | — | — | — | — | 33% | 33% | 25% | — |
|  |  | Xylooligosaccharide | — | — | — | — | — | 33% | 33% | 50% | 75% |
|  | Other | Na alginate | — | — | — | 100% | 100% | — | — | — | — |
| Results | Edible harvest (kg/ha) |  | 3760 100% | 4268 114% | 4018 107% | 3220 86% | 3527 94% | 4580 122% | 5193 138% | 4870 130% | 4830 128% |
|  | Sugar content |  | 6.20% 100% | 6.46% 104% | 7.07% 114% | — — | — — | 7.81% 126% | 6.77% 109% | 7.32% 118% | 7.41% 120% |

4. Measurement of Tomato Plant Dry Weight (1) Preparation of Plant Vitalizer

Each oligosaccharide prepared in [1. Preparation of oligosaccharide] was dissolved in water while stirring with a stirrer in a compositional ratio to 1000 times the plant vitalizer concentration (ppm by mass) in Comparative Example 8-12 and Examples 4-5 and 14-15 listed in the tables, after which the bacteria were removed with a 0.45 μm filter, to obtain plant vitalizer stock solutions. The stock solution was diluted 1000-fold with water and used for the following cultivation test.

(2) Cultivation Test

After immersing tomato seeds in distilled water for 6 hours, the horny layer was removed and the seeds were dried in an aerated location for 30 minutes. After then placing 10 seeds each in different culture dishes inlaid with absorbent paper, they were immersed for 6 hours after filling each culture dish with plant vitalizer solution under each of the conditions. Next, 3 seeds of equal size were selected from each culture dish, planted according to the different conditions, and cultivated for 11 days. The plant dry weights of the germinated seeds were measured and compared with the same without application of the plant vitalizer (Comparative Example 7). The plant dry weights were determined by cutting the root parts, directly drying the remaining top parts with a constant temperature dryer for 12 hours at 50° C., and measuring the weights.

TABLE 3

|  |  |  | Comp. Example 7 | Comp. Example 8 | Comp. Example 9 | Comp. Example 10 | Comp. Example 11 | Comp. Example 12 | Example 4 | Example 5 | Example 14 | Example 15 |
|---|---|---|---|---|---|---|---|---|---|---|---|---|
| Conditions | Plant vitalizer concentration (ppm by mass) | | 0 | 100 | 20 | 100 | 20 | 100 | 20 | 100 | 50 | 50 |
|  | Compositional ratio | Exogenous elicitor | Chitin oligosaccharide | — | 100% | — | — | — | — | 33% | 33% | 25% | 25% |
|  |  | Endogenous elicitor | Cellooligo-saccharide | — | — | 100% | 100% | — | — | 33% | 33% | 25% | — |
|  |  |  | Xylooligo-saccharide | — | — | — | — | 100% | 100% | 33% | 33% | 50% | 75% |
|  | Other | Na alginate | — | — | — | — | — | — | — | — | — | — |
| Results | Plant dry weight (mg) | | 38 100% | 64 168% | 42 111% | 50 132% | 60 158% | 63 166% | 67 176% | 66 174% | 65 171% | 64 168% |

5. Evaluation of Komatsuna Elicitor Activity (1) Preparation of Plant Vitalizer

Each oligosaccharide prepared in [1. Preparation of oligosaccharide] was dissolved in water while stirring with a stirrer in a compositional ratio to 1000 times the plant vitalizer concentration (ppm by mass) in Comparative Example 14-16 and Example 6 listed in the tables, after which the bacteria were removed with a 0.45 μm filter, to obtain plant vitalizer stock solutions. The stock solution was diluted 1000-fold with water and used for the following cultivation test.

(2) Preparation of MS Medium

Murashige and Skoog (MS) agar medium was used for raising of the komatsuna. The prepared plant vitalizers were added to the MS medium to the final concentrations indicated for each of the Examples and Comparative Examples, and then autoclaved for 20 minutes at 121° C.

(3) Seeding and Growing Method

High-pressure steam sterilized MS medium was transferred into a plant box on a clean bench and thoroughly cooled, and then komatsuna ("Wakami", Sakata Seed Corp.) were seeded in a count of 10 each. They were then grown for 6 days with long-day conditions of 24 hours in a lighted room at 22° C.

(4) Protein Extraction

A protein extraction buffer with the following composition was prepared.

TABLE 4

| Protein extraction buffer | | |
|---|---|---|
| Reagent name | Volume (mol) | Remark |
| 0.2M phosphate buffer (pH 6.0) | 1.25 ml | |
| 5.0M NaCl | 0.3 ml (150 mM) | |
| 0.5M EDTA 2Na | 20 μl (1 mM) | |
| 60% Glycerol | 1.7 ml | May be 99-100% purity product |
| Triton X-100 | 0.1 ml | Surfactant |
| 1M DTT | 10 μl (1 mM) | |
| 25 × Protease inhibitor | 0.4 ml | 1 Tablet/2 ml $H_2O$ |
| $H_2O$ | 6.22 ml | Ultrapure water |
| Total | 10 ml | |

After adding 300 μl of the prepared protein extraction buffer into a 1.5 ml tube equipped with a Biomasher (Nippi, Inc.), leaves (plant body) sampled and cut with scissors to approximately 4×4 mm were added. The procedure was carried out 5 times for each sample. A stirring rod was then rotated by hand to break up the plant body until the solid portion was generally no longer visible. Centrifugal separation was carried out under conditions of 15,000×g, 10 minutes, 4° C., and the aqueous layer was collected into a fresh 1.5 ml tube to prepare a liquid extract.

(5) Adjustment of Protein Concentration

A 2 mg/ml portion of bovine serum albumin (BSA) of known purity was serially diluted (½, ¼, ⅛, 1/16, 1/32 and 1/64 dilution) to prepare standards. The prepared standards were used to determine the average absorbance at 600 nm (Abs600), and a calibration curve was drawn (n=3). After injecting 300 μl of Coomassie Brilliant Blue (CBB) solution into a 96-well plate, 6 μl of the prepared liquid extract was added. The Abs600 was then measured.

The blank used was MilliQ. The absorbance of the liquid extract was fitted onto the calibration curve drawn with the 2 mg/ml of serially diluted BSA, to determine the protein concentration.

When the measured Abs600 value of the liquid extract fell outside of the calibration curve, it was measured again with appropriate dilution using ultrapure water (MilliQ) to determine the protein concentration.

Dilution was carried out to a constant liquid extract concentration using the determined values, and the diluted extract was used for the following glucanase activity measurement.

(6) Glucanase Activity Measurement

In a 1.5 ml tube there were mixed 100 µl of a B-HS substrate solution prepared by suspending one tablet of B-HS reagent (Megazyme Co.) in 10 ml of MilliQ, 50 µl of 0.2 M phosphate buffer solution (pH 6.0) and 50 µl of the previously prepared diluted solution or ultrapure water (blank), to prepare samples for each of the Comparative Examples and Examples. Enzyme reaction was conducted for 1 hour and 30 minutes in a water bath at 30° C., shaking the sample well every 15 minutes. A 100 µl portion of 0.2 N NaOH as reaction stop solution (total: 300 µl) was added to stop the reaction. Centrifugal separation was carried out under conditions of 15,000 rpm, 5 minutes, 200 µl of the supernatant was dispensed into a 96-well plate, and the absorbance at 590 nm (Abs590) was measured to evaluate the glucanase activity, comparing it with the same without application of the plant vitalizer (Comparative Example 13).

TABLE 5

|  |  |  | Comp. Example 13 | Comp. Example 14 | Comp. Example 15 | Comp. Example 16 | Example 6 |
|---|---|---|---|---|---|---|---|
| Conditions | Plant vitalizer concentration (ppm by mass) |  | 0 | 10 | 10 | 10 | 10 |
|  | Compositional ratio | Exogenous elicitor | Chitin oligosaccharide | — | 100% | — | — | 33% |
|  |  | Endogenous elicitor | Cellooligosaccharide | — | — | 100% | — | 33% |
|  |  |  | Xylooligosaccharide | — | — | — | 100% | 33% |
| Results | Elicitor activity |  | 22 | 62 | 29 | 56 | 100 |
|  |  |  | 100% | 282% | 132% | 255% | 455% |

6. Evaluation of Cotton Elicitor Activity (1) Preparation of Plant Vitalizer

Each oligosaccharide prepared in [1. Preparation of oligosaccharide] was dissolved in water while stirring with a stirrer in a compositional ratio to 1000 times the plant vitalizer concentration (ppm by mass) in Examples 7-8 and 16-18 listed in the tables, after which the bacteria were removed with a 0.45 µm filter, to obtain plant vitalizer stock solutions. The stock solution was diluted 1000-fold with water and used for the following cultivation test.

(2) Seeding and Growing Method

A cultivation test was carried out for menka cotton in a planter (640×220×180 mm) containing hilling soil (organic vegetable soil: Hirota Shoten) and fertilizer (New Taki Organic Liquid Fertilizer No. 3: Taki Chemical Co., Ltd.). First, menka cotton from China was seeded, and after germination the tops were sprayed with 50 ml of the prepared plant vitalizer, dispersing it and causing growth. About 1.5 L of 200-fold diluted fertilizer was added to the planter on the day before plant vitalizer dispersion.

(3) Glucanase Activity Measurement

The glucanase activity of the cotton was measured by the same method as in [5. Komatsuna elicitor activity test], and compared with the same without application of the plant vitalizer (Comparative Example 17).

TABLE 6

|  |  |  | Comp. Example 17 | Example 7 | Example 8 | Example 16 | Example 17 | Example 18 |
|---|---|---|---|---|---|---|---|---|
| Conditions | Plant vitalizer concentration (ppm by mass) |  | 0 | 100 | 100 | 100 | 100 | 100 |
|  | Compositional ratio | Exogenous elicitor | Chitin oligosaccharide | — | 33% | 50% | 50% | 25% | 25% |
|  |  | Endogenous elicitor | Cellooligosaccharide | — | 33% | — | 50% | 25% | — |
|  |  |  | Xylooligosaccharide | — | 33% | 50% | — | 50% | 75% |
| Results | Elicitor activity |  | 25 | 100 | 88 | 86 | 92 | 82 |
|  |  |  | 100% | 400% | 350% | 344% | 368% | 328% |

The invention claimed is:

1. A plant vitalizer comprising:
   i) chitin oligosaccharide; and
   ii) at least one oligosaccharide selected from the group consisting of cellooligosaccharide and xylooligosaccharide,
   wherein the chitin oligosaccharide is a chemically or enzymatically modified chitin oligosaccharide;
   a mass ratio of the chemically or enzymatically modified chitin oligosaccharide with respect to the at least one oligosaccharide in the plant vitalizer is 0.2 to 5, and
   the plant vitalizer is in a form of liquid.

2. The plant vitalizer according to claim 1, wherein the total content of the chemically or enzymatically modified chitin oligosaccharide and the at least one oligosaccharide in the plant vitalizer is 0.05 to 10 mass %.

3. The plant vitalizer according to claim 1, which comprises both a cellooligosaccharide and a xylooligosaccharide.

4. The plant vitalizer according to claim 1, which further comprises a spreading agent.

5. The plant vitalizer according to claim 1, where when cellooligosaccharide is present in the plant vitalizer, the cellooligosaccharide is a chemically or enzymatically modified cellulose, and
   wherein when xylooligosaccharide is present in the plant vitalizer, the xylooligosaccharide is a chemically or enzymatically modified xylan.

6. The plant vitalizer according to claim 1, where the mass ratio of the chemically or enzymatically modified chitin oligosaccharide with respect to the at least one oligosaccharide in the plant vitalizer is 0.3 to 1.

7. A fertilizer composition comprising the plant vitalizer according to claim 1.

8. A method, comprising: applying the plant vitalizer according to claim 1 to a plant.

9. The method according to claim 8, which comprises applying the plant vitalizer to a plant at a concentration so that the total content of the chemically or enzymatically modified chitin oligosaccharide and the at least one oligosaccharide is 0.1 to 500 ppm by mass.

10. The method according to claim 8, wherein the plant vitalizer is applied to the plant by foliar application.

11. A method of producing a plant or a part thereof having increased elicitor activity compared to the same without application of the plant vitalizer according to claim 1, wherein the method comprises cultivating the plant or the part thereof by applying the plant vitalizer to the plant or the part thereof.

12. The method according to claim 11, wherein the elicitor activity is determined by measuring glucanase production in the plant.

* * * * *